United States Patent
Hu et al.

(10) Patent No.: US 9,351,952 B2
(45) Date of Patent: May 31, 2016

(54) USE OF HESPERETIN

(75) Inventors: Liu Hu, Zhejiang (CN); Hongying Lan, Zhejiang (CN)

(73) Assignee: NATURAL MEDICINE INSTITUTE OF ZHEJIANG YANGSHENGTANG CO., LTD., Zhejiang (CN)

( * ) Notice: Subject to any disclaimer, the term of this patent is extended or adjusted under 35 U.S.C. 154(b) by 0 days.

(21) Appl. No.: 13/810,828

(22) PCT Filed: Jun. 15, 2011

(86) PCT No.: PCT/CN2011/075765
§ 371 (c)(1),
(2), (4) Date: Feb. 5, 2013

(87) PCT Pub. No.: WO2012/010022
PCT Pub. Date: Jan. 26, 2012

(65) Prior Publication Data
US 2013/0131160 A1     May 23, 2013

(30) Foreign Application Priority Data

Jul. 20, 2010 (CN) .......................... 2010 1 0231389

(51) Int. Cl.
| | | |
|---|---|---|
| A61K 31/352 | (2006.01) | |
| A61K 36/74 | (2006.01) | |
| A61K 36/752 | (2006.01) | |
| A61K 8/49 | (2006.01) | |
| A61Q 19/00 | (2006.01) | |
| A61K 8/97 | (2006.01) | |
| A61K 9/00 | (2006.01) | |
| A61K 47/10 | (2006.01) | |
| A61K 9/06 | (2006.01) | |

(52) U.S. Cl.
CPC ............... *A61K 31/352* (2013.01); *A61K 8/498* (2013.01); *A61K 8/97* (2013.01); *A61K 36/74* (2013.01); *A61K 36/752* (2013.01); *A61Q 19/00* (2013.01); *A61K 9/0014* (2013.01); *A61K 9/06* (2013.01); *A61K 47/10* (2013.01)

(58) Field of Classification Search
CPC ........................ A61K 31/352; A61K 36/752
See application file for complete search history.

(56) References Cited

U.S. PATENT DOCUMENTS 5,587,176 A * 12/1996 Warren et al. ................ 424/443
2010/0098751 A1 * 4/2010 Dumas et al. ................ 424/450

FOREIGN PATENT DOCUMENTS

| EP | 1216696 B1 * | 12/2001 |
|---|---|---|
| FR | 2 834 639 | 7/2003 |
| JP | 2001-72564 | 3/2001 |
| JP | 2001-072564 | 3/2001 |
| JP | 2010-30967 | 2/2010 |
| JP | 2010-31005 | 2/2010 |
| WO | WO 2009/116450 | 9/2009 |
| WO | WO 2009/127058 | 10/2009 |

OTHER PUBLICATIONS

Itoh et al ("Effects of Unripe Citrus hassaku Fruits Extract and Its Flavanone Glycosides on Blood Fluidity." Biol Pharm Bull. 2010; 33(4):659-664, published online Jan. 19, 2010).*
Taxon: Citrus hassaku hort. ex Tanaka, USDA—GRIN—May 22, 1997.*
Tsai et al ("In vitro permeation and in vivo whitening effect of topical hesperetin microemulsion delivery system." International Journal of Pharmaceutics, 2010; 388:257-262).*
Cetanol (SciFinder CAS Registry No. 36653-82-4, 2014).*
dimethyl disiloxane (SciFinder CAS Registry No. 9016-00-6, 2014).*
B. Kamins (B. Kamins Therapeutic Eye Cream, http://www.skinstore.com/p-1827-b-kamins-therapeutic-eye-cream.aspx, Internet Archive Wayback Machine date, Nov. 8, 2008).*
Ex parte Francine Gervais and Louis R. Lamontagne, Appeal No. 2012-002886.*
Taiwanese Office Action dated Apr. 19, 2013 for Appln No. 100125641.
International Search Report for PCT/CN2011/075765.
Taiwanese Office Action dated Jan. 6, 2014 for Appln No. 100125641.
Yue et al.; "Effect of topical application of hesperidin, aescin and tanshinone of finger nailfold skin microcirculation"; Journal of Clinical Dermatology, 2005.
Perrier; Fragrance Journal 2004, vol. 8, pp. 88-93.
Mishra et al. "Production and characterization of Hesperetin nanosuspension for dermal delivery", International Journal of Pharmaceutics, 2009, pp. 182-189.
Huang et al.; "The effect of Component of Cream for Topical Delivery of Hesperetin", Chem Pharm Bull; 2010, vol. 58, No. 5, pp. 611-614.
Taiwanese Office Action dated Jan. 14, 2015 for Appln No. 100125641.

* cited by examiner

*Primary Examiner* — Marcos Sznaidman
*Assistant Examiner* — Rayna B Rodriguez
(74) *Attorney, Agent, or Firm* — Pillsbury Winthrop Shaw Pittman, LLP

(57) ABSTRACT

The present invention discloses a use of hesperetin or a hesperetin-containing plant extract in the manufacture of a product for improving and/or promoting skin microcirculation, or for eliminating and/or alleviating diseases or conditions associated with poor skin microcirculation. The present invention also discloses a composition comprising an effective amount of hesperetin or a hesperetin-containing plant extract, and to a method for improving and/or promoting skin microcirculation, or eliminating and/or alleviating diseases or conditions associated with poor skin microcirculation, by using hesperetin. The skin microcirculation of the present invention is preferably eye skin microcirculation.

2 Claims, No Drawings

USE OF HESPERETIN

CROSS-REFERENCE TO RELATED APPLICATIONS

This is the U.S. National Stage of PCT/CN2011/075765, filed Jun. 15, 2011, which in turn claims priority to Chinese Patent Application No. 201010231389.2, filed Jul. 20, 2010, the entire contents of all applications are incorporated herein by reference in their entireties.

TECHNICAL FIELD

The present invention relates to a novel use of hesperetin, particularly, a novel use in cosmetics, more particularly, a use of hesperetin as a chemical ingredient for improving skin microcirculation, in particular, a use in dispelling under-eye dark circle.

BACKGROUND ART

Eye skin in human bodies is different from skin of other parts in human bodies in structure. Firstly, the skin around eyes, which is above zygoma and in the flanks of nose bridge, is "transportaion sites" of blood vessels and lymph. In this region, face venules converge, and blood vessels are fine and abundant. If eye skin microcirculation is deficient, it will lead to poor blood circulation or tissue edema resulting in blood stasis and hematoma, water hoarding. Meanwhile, skin around eyes is very thin, only 1/10 thickness of skin of other parts, and therefore the skin around eyes exhibits atropurpureus and forms under-eye dark circle easily after light reflection. Moreover, factors, such as fatigue, pressure, and sleep insufficiency, are important factors responsible for microcirculation dysfunction. As growing older, the thickness of skin decreases by about 6% per 10 years, and therefore under-eye dark circle is more obvious. Thus, no matter for a short or long term, women in different ages experienced to be perplexed or are perplexed all the time by under-eye dark circle, and need to be improved by improving microcirculation of skin around eyes.

It is reported in papers that many natural plants extracts can significantly improve skin microcirculation after administering them by routes, such as, orally and intravenously, wherein the natural plants extracts include, for example, extract of safflower, extract of *salvia miltiorrhiza*, extract of ginkgo leaf, extract of *Ruscus aculeatus* L., extract of genista, extract of oranges and tangerines, extract of ginseng, and the like. Some papers also reported the effect of some monomeric ingredients extracted from said plant extracts, such as tanshinone, ginsenoside, β-aescin, ruscogenin, ginkgo flavone, and the like, on microcirculation after topical application of them to human skin. However, the results show that these chemical substances cannot significantly improve skin microcirculation after topical administration of them to skin surface.

Eye products for improving skin microcirculation (for example, improving eye skin microcirculation such as dispelling under-eye dark circle), as sold in market currently, emerge endlessly, most of which have some plant extracts added. However, on one hand, it is not clear which ingredient of the extracts or which class of ingredients of the extracts work, on the other hand, these products do not have a significant effect on dispelling under-eye dark circle. Most products for improving skin microcirculation (for example, for dispelling under-eye dark circle) did not bring about the effect as expected (such as the efficacy of dispelling under-eye dark circle) after being used by the consumers. Therefore, it is still a major research direction for the skilled in the art to look for chemical substances capable of improving skin microcirculation significantly after topical application, so as to develop products for improving skin microcirculation (for example, for improving eye skin microcirculation, such as, for dispelling under-eye dark circle), in particular, eye care products for dispelling under-eye dark circle.

Hesperetin is a flavanone, derived from pericarp or fruits of citrus plants of Rutaceae, with a formula as follows:

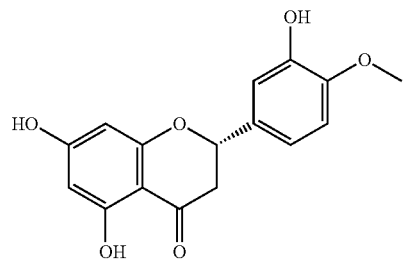 [SMILES: COc1ccc([C@@H]2CC(=O)c3c(O)cc(O)cc3O2)cc1O]

It has a molecular weight of 610.57 and is light yellow acicular crystal at room temperature. Hesperetin, as an important active substance in Chinese herbs, has many important biological and pharmaceutical activities, mainly including anti-oxidation, anti-inflammation, reducing blood fat, cardiovascular protection, anti-cancer effect, and the like. However, it is not reported yet that hesperetin is useful in improving skin microcirculation. Development of new products capable of improving skin microcirculation, particularly products capable of improving eye skin microcirculation, is still expected by a person skilled in the art.

CONTENTS OF THE INVENTION

The objective of the present invention is to provide a novel use of hesperetin in improving skin microcirculation (for example, improving eye skin microcirculation such as dispelling under-eye dark circle). It is discovered in the present invention surprisingly that hesperetin or a hesperetin-containing plant extract effectively improves skin microcirculation, particularly eye skin microcirculation, more particularly effectively dispels under-eye dark circle. The present invention is accomplished on the basis of above discovery.

SUMMARY OF THE INVENTION

Thus, in a first aspect, the present invention provides a use of hesperetin or a hesperetin-containing plant extract in the manufacture of a product for improving and/or promoting skin microcirculation, or for eliminating and/or alleviating diseases or conditions associated with poor skin microcirculation.

The use according to the first aspect of the present invention, wherein the skin microcirculation is eye skin microcirculation.

The use according to the first aspect of the present invention, wherein the diseases or conditions associated with poor skin microcirculation are diseases or conditions associated with poor eye skin microcirculation.

The use according to the first aspect of the present invention, wherein the diseases or conditions associated with poor eye skin microcirculation are under-eye dark circles.

The use according to the first aspect of the present invention, wherein the hesperetin-containing plant extract is an extract obtained by extracting from pericarp and/or fruits of citrus plants of Rutaceae or from aerial part of *Galium mollugo* linn.

The use according to the first aspect of the present invention, wherein the hesperetin-containing plant extract is an extract obtained by extracting from pericarp and/or fruits of citrus plants of Rutaceae or from aerial part of *Galium mollugo* linn., and the extract comprises hesperetin in an amount of not less than 50 wt % (weight %). In a preferred embodiment, the extract comprises hesperetin in an amount of 60 wt % or more, 70 wt % or more, 80 wt % or more, 85 wt % or more, 90 wt % or more, or 95 wt % or more.

The use according to the first aspect of the present invention, wherein the product is a product for topical administration.

The use according to the first aspect of the present invention, wherein the product is a topical administration product for external skin use.

The use according to the first aspect of the present invention, wherein the product is a topical administration product for eye skin.

The use according to the first aspect of the present invention, wherein the product is a cosmetic.

The use according to the first aspect of the present invention, wherein the product is in a form of solution, emulsion, paste, cream, or gel.

The use according to the first aspect of the present invention, wherein the product comprises (1) hesperetin or a hesperetin-containing plant extract, and (2) a physiologically acceptable excipient.

The use according to the first aspect of the present invention, wherein the product comprises (1) hesperetin or a hesperetin-containing plant extract, and (2) a physiologically acceptable excipient; wherein the hesperetin or the hesperetin-containing plant extract accounts for 0.01 to 20 wt % of the total weight of the product, as calculated by weight of hesperetin. In an embodiment, the hesperetin or the hesperetin-containing plant extract accounts for 0.05 to 15 wt %, 0.1 to 10 wt %, 0.2 to 10 wt %, or 0.2 to 5 wt % of the total weight of the product, as calculated by weight of hesperetin.

In a second aspect, the present invention provides a composition, comprising (1) an effective amount of hesperetin or a hesperetin-containing plant extract, and optionally (2) a physiologically acceptable excipient.

The composition according to the second aspect of the present invention, comprises: (1) an effective amount of hesperetin or a hesperetin-containing plant extract, and optionally (2) a physiologically acceptable excipient; wherein the hesperetin or the hesperetin-containing plant extract accounts for 0.01 to 20 wt % of the total weight of the composition, as calculated by weight of hesperetin. In an embodiment, the hesperetin or the hesperetin-containing plant extract accounts for 0.05 to 15 wt %, 0.1 to 10 wt %, 0.2 to 10 wt %, or 0.2 to 5 wt % of the total weight of the composition, as calculated by weight of hesperetin.

The composition according to the second aspect of the present invention, wherein the hesperetin-containing plant extract is an extract obtained by extracting from pericarp and/or fruits of citrus plants of Rutaceae or from aerial part of *Galium mollugo* linn.

The composition according to the second aspect of the present invention, wherein the hesperetin-containing plant extract is an extract obtained by extracting from pericarp and/or fruits of citrus plants of Rutaceae or from aerial part of *Galium mollugo* linn., and the extract comprises hesperetin in an amount of not less than 50 wt %. In a preferred embodiment, the extract comprises hesperetin in an amount of 60 wt % or more, 70 wt % or more, 80 wt % or more, 85 wt % or more, 90 wt % or more, or 95 wt % or more.

The composition according to the second aspect of the present invention, is a product improving and/or promoting skin microcirculation, or for eliminating and/or alleviating diseases or conditions associated with poor skin microcirculation. In one embodiment, the skin microcirculation is eye skin microcirculation. In one embodiment, the diseases or conditions associated with poor skin microcirculation are diseases or conditions associated with poor eye skin microcirculation. In one embodiment, the diseases or conditions associated with poor eye skin microcirculation are under-eye dark circles.

The composition according to the second aspect of the present invention, is a product for topical administration.

The composition according to the second aspect of the present invention, is a topical administration product for external dermatological use.

The composition according to the second aspect of the present invention, is a topical administration product for eye skin.

The composition according to the second aspect of the present invention, is a cosmetic.

The composition according to the second aspect of the present invention, is in a form of solution, emulsion, paste, cream, or gel.

In a third aspect, the present invention provides a method for improving and/or promoting skin microcirculation, or for eliminating and/or alleviating diseases or conditions associated with poor skin microcirculation in a subject in need thereof, comprising administering an effective amount of hesperetin or a hesperetin-containing plant extract to the subject.

The method according to the third aspect of the present invention, wherein the skin microcirculation is eye skin microcirculation.

The method according to the third aspect of the present invention, wherein the diseases or conditions associated with poor skin microcirculation are diseases or conditions associated with poor eye skin microcirculation.

The method according to the third aspect of the present invention, wherein the diseases or conditions associated with poor eye skin microcirculation is under-eye dark circle.

The method according to the third aspect of the present invention, wherein the hesperetin-containing plant extract is an extract obtained by extracting from pericarp and/or fruits of citrus plants of Rutaceae or from aerial part of *Galium mollugo* linn.

The method according to the third aspect of the present invention, wherein the hesperetin-containing plant extract is an extract obtained by extracting from pericarp and/or fruits of citrus plants of Rutaceae or from aerial part of *Galium mollugo* linn., and the extract comprises hesperetin in an amount of not less than 50 wt %. In a preferred embodiment, the extract comprises hesperetin in an amount of 60 wt % or more, 70 wt % or more, 80 wt % or more, 85 wt % or more, 90 wt % or more, or 95 wt % or more.

The method according to the third aspect of the present invention, wherein the effective amount of hesperetin or a hesperetin-containing plant extract is administered in a form of a topical administration product.

The method according to the third aspect of the present invention, wherein the effective amount of hesperetin or a hesperetin-containing plant extract is administered in a form of a topical administration product for external dermatological use.

The method according to the third aspect of the present invention, wherein the effective amount of hesperetin or a hesperetin-containing plant extract is administered in a form of a topical administration product for eye skin.

The method according to the third aspect of the present invention, wherein the effective amount of hesperetin or a hesperetin-containing plant extract is administered in a form of cosmetic.

The method according to the third aspect of the present invention, wherein the effective amount of hesperetin or a hesperetin-containing plant extract is administered in a form of solution, emulsion, paste, cream, or gel.

The features of any aspect of the present invention or of any embodiment of the aspect are also applicable to any other embodiment of the aspect or to any other aspect or any embodiment of the another aspect.

DETAILED DESCRIPTION OF THE INVENTION

The aspects and characteristics of the present invention are further described as follows.

All the documents cited in the present invention are incorporated herein by reference in its entirety, and if the meanings expressed in the documents are different from those in the present invention, the expressions in the present invention will control. In addition, the terms and phases used in the present invention have the general meanings recognized by a person skilled in the art. Even so, the present invention still tries to expound and explain the terms and phases as detailed as possible. If the terms and phases mentioned herein are not consistent with the well-known meanings, the meanings expressed in the present invention will control.

As described herein, the term "skin microcirculation" refers to microvascular net under dermal layer of skin, which is a terminal part of circulation, belongs to blood capillary, is a connection point between artery and vein, and is a place where material interchange of blood and tissue cells is carrier out. Skin microcirculation is a complex dynamic system, which has an important effect on skin color, temperature adjustment, skin metabolism and transdermal transport, and therefore directly affects the health of skin.

As described herein, the term "diseases or conditions associated with poor skin microcirculation" refers to pathogenic or nonpathogenic physical status or abnormal condition resulted from poor topical skin microcirculation or topical skin microcirculation disorder, such as, dermatitis, pigmentation, skin aging, pale skin, bloodshot on face, topical skin stasis and hematoma, topical water hoarding, and under-eye dark circle.

As described herein, the term "improving", "promoting", "eliminating", and "alleviating", for example, in the expressions "improving and/or promoting skin microcirculation" and "for eliminating and/or alleviating diseases or conditions associated with poor skin microcirculation" as described herein, refers to the generation of a beneficent effect on pathogenic or nonpathogenic physical status or abnormal condition resulted from poor topical skin microcirculation or topical skin microcirculation disorder, for example, improvement of topical skin microcirculation, promotion of topical skin microcirculation, elimination of pathogenic or nonpathogenic physical status or abnormal condition resulted from poor topical skin microcirculation or topical skin microcirculation disorder, and alleviation of pathogenic or nonpathogenic physical status or abnormal condition resulted from poor topical skin microcirculation or topical skin microcirculation disorder, for example, improvement of bloodshot eyes, elimination of pigmentation, eliminating hydroncus, alleviation of stasis and hematoma, elimination of under-eye dark circle, and the like.

As described herein, the term "physiologically acceptable" means that substances are physiologically compatible, particularly, may be used in a product for external dermatological use when contacting skin, for example, without bringing about side effects such as irritability to skin. Particularly, for example, diluents, surfactants, thickeners, emollients, etc. may be used in cosmetics.

As described herein, the term "an effective amount" refers to an dose that can accomplish the treatment, prevention, reduction and/or alleviation of the diseases or conditions of the present invention in a subject.

As described herein, the term "composition" also refers to "cosmetic", "cosmetic composition", "pharmaceutical composition", all of which may be used in individuals for the treatment, prevention, reduction and/or alleviation of the diseases, conditions, or physical status of the present invention.

As described herein, the term "individual" may further refer to "subject", "patient" or other animal which are administered with the composition of the present invention to improve and/or promote the skin microcirculation appeared in them or to eliminate and/or alleviate diseases or conditions associated with poor skin microcirculation appeared in them, particularly, mammal, such as human, dog, monkey, bovine, horse, etc., in particular, human.

As described herein, the term "eye skin microcirculation" refers to microcirculation of skin around eyes.

According to the present invention, the hesperetin may be extracted from pericarp or fruits of citrus plants of Rutaceae or from aerial part of *Galium mollugo* linn. or may be synthesized by chemical methods known in the art or be obtained by biotransformation. The hesperetin may be a pure compound, or an extract containing hesperetin in an amount of not less than 50%. In the present invention, as calculated by the weight of pure compound of hesperetin, the hesperetin is present in a concentration of 0.01%-20%, preferably 0.05%-15%, most preferably 0.1%-10% in the composition of the present invention.

The present invention also comprises a cosmetic skin care composition comprising hesperetin.

The present invention relates to a cosmetic skin care composition, comprising (1) hesperetin present in an amount of 0.1%-10% by weight; and (2) cosmetically acceptable vehicles.

The hesperetin used in the composition of the present invention is to achieve the effect of dispelling under-eye dark circle.

The composition and method of the present invention further comprises cosmetically acceptable vehicles as the diluents, dispersants or carriers of active ingredient in the composition, to promote the distribution of the composition when applying the composition to skin.

Vehicles other than water comprise liquid or solid emollients, surfactants, solvents, and thickeners.

Active ingredients of various types may be present in the cosmetic composition of the present invention. Active substances are defined as substances different from emollients and ingredients merely improving physical properties of the composition.

In accordance with the present invention, under-eye dark circle may be reduced or eliminated by topical application of hesperetin.

The present invention relates to a novel use of hesperetin in cosmetics, particularly a novel use of hesperetin as a chemical ingredient for improving skin microcirculation in dispelling under-eye dark circle. Preferably, in the use, the hesperetin is present in amount of 0.01%-10% by weight of the composition.

For better utilization of hesperetin, the present invention studies the effect of topical administration of hesperetin to skin surface on promoting microcirculation. The results show that after topical application of hesperetin, skin microcirculation is significantly improved. The applicant applied hesperetin to eye care products and found that it could significantly dispel under-eye dark circle.

SPECIFIC MODES FOR CARRYING OUT THE INVENTION

The present invention is further described by the following examples. However, the scope of the present invention is not limited to the following examples. The skilled in the art could understand that any change and modification may be made to the present invention without departing from the spirit and scope of the present invention.

The present invention generally and/or specifically describes the materials and experimental methods used in the present invention. Although many materials and operation methods used for achieving the purpose of the present invention are well known in the art, the present invention, still describe them as detailed as possible. In the following examples, unless indicated otherwise, % represent wt %, i.e. percentage by weight.

Example 1

Observing the Effect of Topical Application of Hesperetin on Skin Microcirculation by Laser Doppler The experimental method for promoting microcirculation: Male *Oryctolagus cuniculus* weighted 3.0-3.5 kg were used. After shaving the hair on the back of the *Oryctolagus cuniculus*, 10 points for testing blood flow were marked with a marker pen on the hairless skin of the rabbit, i.e. 5 points for each of the right side and the left side, and aorta was avoided when drawing the points. Before smearing the sample, the basic values of blood flow at the 10 points of rabbits of each experimental group were determined by Laser Doppler Flowmetery. The rabbits of each group had blank solution smeared on the left back and had a hesperetin-containing solution smeared on the right back (for three groups of animals, the concentration of the solutions were 0.5%, 1% and 2%, respectively, 0.1 ml for each animal), three rabbits were used in parallel for each concentration. 2% solution was orally administrated by a similar method in a volume 100 times compared to the volume used in the group wherein the 2% solution was administered by smearing. After administration, the blood flow value was determined every hour at the same point by Laser Doppler Flowmetery for 24 h, and the variation index of blood flow was calculated to evaluate the effect of hesperetin on the back blood of rabbits, wherein a higher variation index of blood flow indicates a better effect of promoting microcirculation. The experimental results were statistically analyzed by SPSS11.5 software, t-test was applied to the measured data to evaluate the experimental results. When $P<0.1$, the data may be regarded as statistically significant. In the results of Table 1, all the time points at with $P<0.1$ in the 24-h test were listed.

TABLE 1

The effect of hesperetin at different concentrations on promoting skin microcirculation in domestic rabbits

| Hesperetin concentration | Working time point | P value as compared to the blank side |
|---|---|---|
| 0.5%, smearing | 1 h | $p < 0.05$ |
| 1%, smearing | 2 h | $p < 0.05$ |
|  | 3 h | $p < 0.05$ |
| 2%, smearing | 1 h | $p < 0.01$ |
|  | 3 h | $p < 0.05$ |
|  | 4 h | $p < 0.05$ |
|  | 5 h | $p < 0.05$ |
|  | 6 h | $p < 0.05$ |
| 2%, orally | — | — |

Note:
"—" represents the time point at which $P < 0.1$ did not appear during the 24 h test.

The experimental results showed that after smearing the backs of rabbits with samples comprising different concentrations of hesperetin, blood flow in skin microvessels was significantly enhanced in rabbits, as compared to the blank side.

Example 2

The Effect of Hesperetin on Dispelling Under-Eye Dark Circle

Method: 8-week comparison experiments of two formulations at two sides of eyes were used in the study.

In the study, 50 volunteers with medium and severe under-eye dark circle were recruited in the study, to allow the effective number of each paired comparison group to be 15. The subjects were randomly assigned and the compositions were used in the left/right side equivalently, wherein one side of the eyes was smeared with the composition comprising hesperetin, and the other side of the eyes was smeared with the composition comprising no hesperetin, for 8 weeks. Efficacy evaluation was made as to the effect of dispelling under-eye dark circle at Week 0 (before treatment), 2, 4, 6 and 8.

Efficacy evaluation method: A photo of eyes of the subject taken at Day 0 of the experiment was used as the baseline data, and photos were taken at Week 2, 4, 6 and 8 of the experiment. Lab system of photoshop software was used to calculate and analyze the colority, wherein L represented the white degree of eye skin, a higher L value indicated a whiter skin. After comparison with the baseline data, SPSS statistic data was used to evaluate the efficacy of the products. When $P<0.1$, the data may be regarded as statistically significant.

The basic formulations in Table 2 and the compositions in Table 3 were used in the subjects for test.

TABLE 2

Basic formulations

| Ingredients | weight/weight |
|---|---|
| Methyl glucose sesqui-stearate | 1.2% |
| dimethyl siloxane | 1.0% |
| cetanol/octadecanol | 3% |
| Dicapryl carbonate | 4% |
| propyl heptyl octanoate | 2% |
| lecithin | 2.5% |
| Xanthan Gum | 0.3% |
| 1,3-butanediol | 4% |
| EDTA-2Na | 0.2% |
| glycerin | 2.0% |

TABLE 2-continued

Basic formulations

| Ingredients | weight/weight |
|---|---|
| triethanolamine | 2% |
| Lactic acid | an appropriate amount |
| preservative | an appropriate amount |
| water | added to 100% |

TABLE 3

Composition

| Composition | Ingredients |
|---|---|
| 1 | basic formulation |
| 2 | basic formulation +0.5% hesperetin |
| 3 | basic formulation +2.0% hesperetin |
| 4 | basic formulation +10.0% hesperetin extract (comprising 50% hesperetin) |

The following paired comparisons were carried out:
Paired comparison 1: Composition 1 (basic formulation) vs Composition 2 (basic formulation+0.5% hesperetin);
Paired comparison 2: Composition 1 (basic formulation) vs Composition 3 (basic formulation+2% hesperetin);
Paired comparison 3: Composition 1 (basic formulation) vs Composition 4 (basic formulation+10% hesperetin extract).
The results were listed in Tables 4A to 4C:

TABLE 4A

The average improvement of under-eye dark circle by Paired comparison 1

| Week | basic formulation # | basic formulation +0.5% hesperetin |
|---|---|---|
| 0 | 0 | 0 |
| 2 | 1.7% | 1.5% |
| 4 | 1.8% | 2.0% |
| 6 | 1.2% | 2.0%** |
| 8 | 1.5% | 2.8%** |

**basic formulation +0.5% hesperetin provided a significantly greater improvement than basic formulation after using it for 6 weeks ($P < 0.05$).

basic formulation without active ingredient also generated a change, the accuracy of the experiments would be enhanced by deduction of the change. The factors responsible for the change generated by basic formulation might include, but be not limited to, non-objective factors such as the stimulating effect of the basic formulation itself, stimulation by heat and cold, emotion, and luminance of the photographic environment. These factors might be responsible for a change in L value, thereby reducing the objectivity of the experimental results. Thus, experimental conditions should be stringently controlled during the experiment. In the experimental method, self-control was set in the right and left eyes so as to eliminate or balance the effect of unrelated variants during the experiment to the maximum extent. Therefore, the difference between the experimental group and the control group might be regarded as the effect resulted from the experimental variants. For example, in the Example, the experimental results showed that the L value, on the side where basic formulation was smeared, increased to different extents at different times in the test, indicating that non-objective factors had a certain effect on the L value under the experimental conditions. However, the L value, on the side where hesperetin was smeared, increased to a larger extent and was significant as compared to the former, indicating the significance is resulted from hesperetin.

TABLE 4B

The average improvement of under-eye dark circle by Paired comparison 2

| Week | basic formulation | basic formulation +2% hesperetin |
|---|---|---|
| 0 | 0 | 0 |
| 2 | 1.7% | 2.9%** |
| 4 | 1.1% | 2.3%** |
| 6 | 1.8% | 2.8%** |
| 8 | 1.5% | 3.0%** |

**basic formulation +2% hesperetin provided a significantly greater improvement than basic formulation after using it for 2 weeks ($P < 0.05$).

TABLE 4C

The average improvement of under-eye dark circle by Paired comparison 3

| Week | basic formulation | basic formulation +10% hesperetin extract |
|---|---|---|
| 0 | 0 | 0 |
| 2 | 1.8% | 2.8%** |
| 4 | 2.0% | 3.2%** |
| 6 | 2.2% | 3.5%** |
| 8 | 1.5% | 3.5%** |

**basic formulation +10% hesperetin extract provided a significantly greater improvement than basic formulation after using it for 2 weeks ($P < 0.05$).

Said paired comparison results showed that the composition comprising hesperetin significantly improved under-eye dark circle as compared with the composition comprising no hesperetin. The Examples indicated that hesperetin was useful for improving skin microcirculation, particularly eye skin microcirculation, in particular, was useful as cosmetic skin care product for dispelling under-eye dark circle.

The above-mentioned examples illustrate the composition for topical application according to the present invention, which may be processed by conventional means. They are suitable for cosmetic skin care use. In particular, the compositions are suitable for dispelling under-eye dark circle to improve appearance and feeling of eye skin.

The invention claimed is:
1. A method for eliminating and/or alleviating under-eye dark circles, comprising:
administering an effective amount of hesperetin or a hesperetin-containing plant extract to the subject,
the hesperetin-containing plant extract being an extract obtained by extracting from pericarp of citrus plants of Rutaceae or from aerial part of *Galium mollugo* linn, the extract comprising hesperetin in an amount of not less than 50 wt %, the hesperetin or a hesperetin-containing plant extract being administered in a form of a topical administration product,
the topical administration product consisting of hesperetin or a hesperetin-containing plant extract, and physiologically acceptable excipients hesperetin or a hesperetin-containing plant extract in an amount of 0.2 to 2 wt % of the total weight of the product, as calculated by weight of hesperetin,
wherein said physiologically acceptable excipients consist of:

| Ingredients | weight/weight |
| --- | --- |
| Methyl glucose sesqui-stearate | 1.2% |
| dimethyl siloxane | 1.0% |
| cetanol/octadecanol | 3% |
| Dicapryl carbonate | 4% |
| propyl heptyl octanoate | 2% |
| lecithin | 2.5% |
| Xanthan Gum | 0.3% |
| 1,3-butanediol | 4% |
| EDTA-2Na | 0.2% |
| glycerin | 2.0% |
| triethanolamine | 2% |
| Lactic acid | an appropriate amount |
| preservative | an appropriate amount |
| water | added to 100%. |

2. A composition consisting of:
hesperetin or a hesperetin-containing plant extract, and physiologically acceptable excipients;
wherein the hesperetin or the hesperetin-containing plant extract accounts for 0.2 to 2 wt % of the total weight of the composition, as calculated by weight of hesperetin, and
wherein the hesperetin-containing plant extract is an extract obtained by extracting from pericarp of citrus plants of Rutaceae or from aerial part of *Galium mollugo* linn, the extract comprising hesperetin in an amount of not less than 50 wt %,
wherein said physiologically acceptable excipients consist of:

| Ingredients | weight/weight |
| --- | --- |
| Methyl glucose sesqui-stearate | 1.2% |
| dimethyl siloxane | 1.0% |
| cetanol/octadecanol | 3% |
| Dicapryl carbonate | 4% |
| propyl heptyl octanoate | 2% |
| lecithin | 2.5% |
| Xanthan Gum | 0.3% |
| 1,3-butanediol | 4% |
| EDTA-2Na | 0.2% |
| glycerin | 2.0% |
| triethanolamine | 2% |
| Lactic acid | an appropriate amount |
| preservative | an appropriate amount |
| water | added to 100%. |

* * * * *